United States Patent [19]

Zieve et al.

[11] Patent Number: 4,756,029
[45] Date of Patent: Jul. 12, 1988

[54] FEMININE URINARY DEVICE

[76] Inventors: Ron Zieve; Terri Zieve, both of 1859 Gramercy Ct., Dunwoody, Ga. 30338

[21] Appl. No.: 93,047

[22] Filed: Sep. 4, 1987

[51] Int. Cl.⁴ .................... A47K 11/00; A47K 11/02
[52] U.S. Cl. ........................... 4/144.4; 4/144.3; 4/144.2; 4/144.1; 604/329
[58] Field of Search ............ 4/144.1, 144.2, 144.3, 4/144.4, 301; 604/329, 330, 347, 350, 331, 354

[56] References Cited

U.S. PATENT DOCUMENTS

| | | | |
|---|---|---|---|
| 2,878,486 | 3/1959 | Bartlett et al. | 4/144.4 |
| 3,964,111 | 6/1976 | Packer | 4/144.4 |
| 3,995,329 | 12/1976 | Williams | 4/144.4 X |
| 4,198,979 | 4/1980 | Cooney et al. | 604/329 |
| 4,531,245 | 7/1985 | Lowd et al. | 4/144.3 |
| 4,626,249 | 12/1986 | Hamey | 4/144.4 X |

Primary Examiner—Henry K. Artis
Attorney, Agent, or Firm—Hurt, Richardson, Garner Todd & Cadenhead

[57] ABSTRACT

A feminine urinary device which permits women, both adults and children, to urinate in a standing position. The urinary device is a disposable substantially flat flexible pad having a hingedly attached flap with expandable side walls to permit the flap to move from a collapsed flat configuration downwardly to an open expanded configuration, forming a conduit for the passing of urine when the pad is held firmly in place by the user and the conduit is aligned with the opening of the urethra. The urinary device can also be constructed by forming an aperture in the pad and attaching thereto an expandable spout to form the conduit.

7 Claims, 1 Drawing Sheet

FEMININE URINARY DEVICE

BACKGROUND OF THE INVENTION

1. Field of the Invention

This invention relates generally to a urinary device and, more specifically to an improved disposable feminine urine conducting device which permits a female to urinate comfortably and hygienically from a standing position.

2. Description of the Prior Art

The female anatomy creates a particularly annoying problem for women of all ages when travelling or enjoying outdoor activities such as camping, hiking, and cross-country skiing, and that is—where to urinate. Public facilities are most often unsanitary and finding a place to squat discreetly outdoors is usually impossible. The fear of becoming infected with the AIDS virus, Herpes, Chlamydia, and other somewhat less devastating microorganisms has altered our sexual and personal hygiene habits more in recent years than ever before. Whether these organisms remain viable and infectious in the environs of the public toilet is debatable, however, women should not have to take unnecessary chances. This dilemma, unique to the female, has been recognized by others and various attempts have been made to provide a urinary device for women. None of these urinary devices, however, have solved the problem of providing a sanitary, disposable urinary conduit that is convenient and comfortable to use, easy to carry, and inexpensive to manufacture.

SUMMARY OF THE INVENTION

As discussed above, a major objective of the present invention is to provide a urinary device that will protect females, adults and children, from exposure to the unsanitary conditions found in public facilities and therefore prevent the spread of contagious diseases.

It is also a major objective of the present invention to provide a disposable urinary device for women that is compact and easy to carry.

Another major objective is to provide a urinary device that is comfortable and hygienic to use.

It is a further objective of this invention to provide a urinary conduit that can be used by women comfortably, while standing, without soiling their clothes.

Another objective is to provide a disposable urinary conduit which is biodegradable.

And yet another objective is to provide a disposable urinary conduit which is easy and inexpensive to manufacture.

An additional objective of the present invention is to provide a disposable urinary device which has a pad of absorbent material for wiping any residual urine from the genitalia, thus eliminating the need for toilet paper.

The above and other objectives have been met by the disposable urinary device of the present invention described briefly as follows:

The urinary device is a flat elongate flexible pad having a top and bottom surface. A longitudinally extending flap is cut into the pad. The flap is hingedly secured at one end while the opposite end is free. The side edges of the flap have expandable side portions which connect with the bottom surface of the pad to permit the flap to go from a collapsed folded configuration to an expanded open configuration to form a urinary conduit when the pad is aligned with the urethra of the female user. The side portions of the flap may be of smooth or accordion-type construction. The top surface of the pad may be provided with a sealing ring extending around the periphery of the opening in the pad. Also, an additional piece of absorbent material may be placed on the top surface of the pad for wiping away residual urine.

DETAILED DESCRIPTION OF THE DRAWINGS

Figure 1:
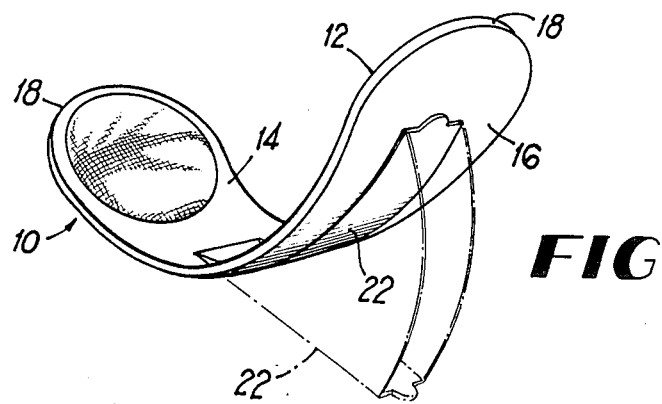
FIG. 1 is a perspective view of the urinary device in its collapsed configuration.
Figure 1A:
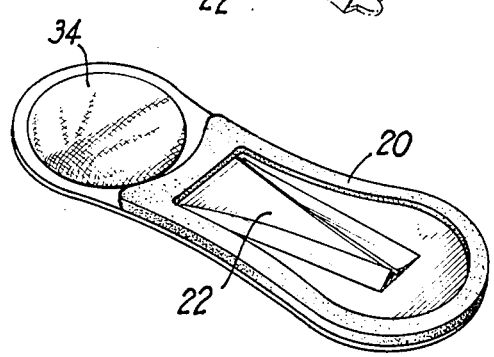
FIG. 1A is a perspective view showing the urinary device with a sealing ring.

FIG. 1 illustrates the urinary device 10 of the present invention in its collapsed or folded configuration. As shown in FIG. 1, the device is a flat flexible pad 12 having a top surface 14 and a bottom surface 16. The ends 18 of pad 12 are preferably constructed having curvilinear configuration to facilitate forming a seal when held firmly in position for use. Also, to this end, pad 12 may have an absorbent sealing gasket 20 positioned on top surface 14 as shown in FIG. 1A.

Figure 2:
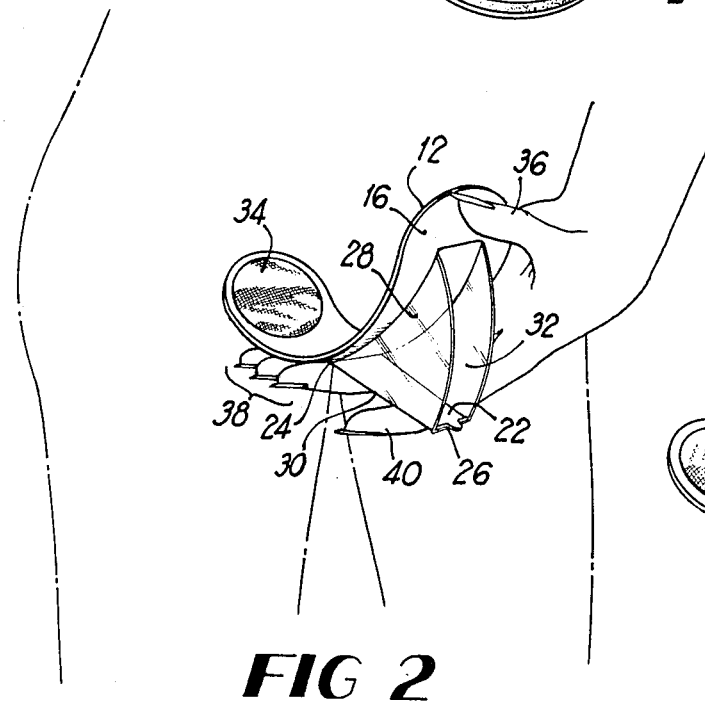
FIG. 2 is a perspective view of the urinary device in its expanded configuration in position for use.

An elongate substantially U-shaped flap 22 is centrally and longitudinally formed in pad 12. FIG. 2 illustrates device 10 in its expanded configuration where it can readily be seen that flap 22 is hingedly secured to pad 12 at one end 24, while the other end 26 is free and unattached. Expandable side portions or walls 28 extend between pad 12 and side edges 30 of the flap 22. When flap 22 is in its expanded configuration, conduit 32 is formed which is defined by flap 22 and side walls 28. Side walls 28 may be constructed of any suitable water repellent material such as plastic or a wax-coated paper.

It is desirable to construct urinary device 10 as a disposable product, therefore, it is preferably made of biodegradable materials that will not create problems should the device be flushed down the toilet after use. Also, because the urinary device is disposable, it should be constructed of compact materials to enable a convenient number of devices to be packaged in a single box. The devices could also be stored in dispensing machines placed in public toilets. Streamlined construction is also important because the urinary devices should fit easily into a purse or pocket. The desired thickness of the folded device 10 should be no more than approximately 1/16 inch.

Urinary device 10 may be constructed having an absorbent pad 34 built into the rearward top surface 14 of pad 13 for wiping away any excess urine from the user. This is particularly desirable when device 10 is being used outdoors where toilet paper is not readily available.

In actual use, as illustrated in FIG. 2, pad 12 is positioned against the perineum and held in place conveniently by hand. This is done by placing thumb 36 forwardly on bottom surface 16 and fingers 38 rearwardly on bottom surface 16 and pressing upwardly deforming pad 12 to the contour of the perineum. When pad 12 is deformed as illustrated, flap 22 extends downwardly in its expanded position to form conduit 32. Conduit 32 is aligned with the urethra, thus enabling the female user to void urine in a comfortable hygienic position. Index finger 40 may be used to ensure the correct positioning of conduit 32. The other hand is free to hold clothing out of the path of the urinary stream.

After voiding has been completed, the user slides the device forward, and if device 10 has been provided with absorbent pad 34, pad 34 absorbs any excess urine present on the user is absorbed thereon. The urinary device 10 can then be discarded, either in trash receptacles or wherever convenient, or flushed away down the toilet.

Figure 3:
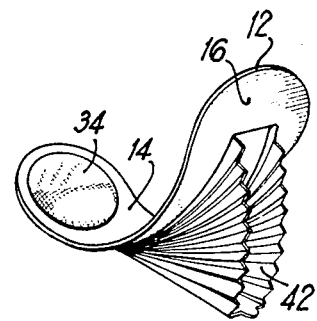
FIG. 3 is an alternate construction of the urinary device showing accordion-type side portions.

Urinary device 10 is economical to manufacture, the flexible pad 12 and flap 22 being constructed from a single piece of absorbent material lined on bottom surface 16 with a sheet of plasticized material. The same plasticized material can be used to make expandable side portions 28 by heat sealing a triangular shaped piece of material between each side edge 30 of flap 22 and bottom surface 16 of pad 12. Side portions 28 can be either a smooth construction as shown in FIG. 2 or an accordion-type construction 42 shown in FIG. 3. The rigidity of the accordian type side portions 42 is sufficient to maintain the flap 22 in its expanded configuration.

It will be understood that the foregoing description is merely illustrative of the invention which is intended to be limited only by the appended claims.

What is claimed is:

1. A urinary device for use by a woman in a standing position comprising a substantially flat elongate flexible pad having a top and bottom surface and a longitudinally extending flap hingedly secured at one end to the pad, the opposite end of the flap being unsecured, the side edges of the flap having expandable side portions that extend between the flap and the pad which are capable of expanding the flap from a collapsed configuration where the flap is in planar alignment with the pad to an open expanded configuration where the flap forms an angle with the planar surface of the pad to form a urine conduit when the top surface of the pad is held firmly in position by the user with the conduit aligned with the opening of the urethra.

2. The device of claim 1 wherein the elongate pad has a curvilinear configuration.

3. The device of claim 1 wherein the expandable side portions have an accordion-type construction.

4. The device of claim 1 further comprising a sealing gasket positioned on the top surface and extending around the flap.

5. The device of claim 1 further comprising the top surface of the pad having an absorbent pad positioned rearwardly from the conduit.

6. The device of claim 1 wherein the pad, flap and expandable side portions are constructed of lightweight, disposable, biodegradable materials.

7. The device of claim 1 wherein the flap is U-shaped.

* * * * *